(12) United States Patent
Liu et al.

(10) Patent No.: US 11,890,254 B2
(45) Date of Patent: Feb. 6, 2024

(54) NECK MASSAGING DEVICE

(71) Applicant: GUANGDONG SKG INTELLIGENT TECHNOLOGY CO., LTD, Shenzhen (CN)

(72) Inventors: Jie Liu, Shenzhen (CN); Hua Xiao, Shenzhen (CN); Xianjie Yu, Shenzhen (CN)

(73) Assignee: GUANGDONG SKG INTELLIGENT TECHNOLOGY CO., LTD, Shenzhen (CN)

( * ) Notice: Subject to any disclaimer, the term of this patent is extended or adjusted under 35 U.S.C. 154(b) by 720 days.

(21) Appl. No.: 16/852,680

(22) Filed: Apr. 20, 2020

(65) Prior Publication Data

US 2020/0237612 A1 Jul. 30, 2020

Related U.S. Application Data

(63) Continuation of application No. PCT/CN2019/075307, filed on Feb. 18, 2019.

(30) Foreign Application Priority Data

Nov. 21, 2018 (CN) .......................... 201811394788.3

(51) Int. Cl.
*A61H 23/02* (2006.01)
*A61N 1/36* (2006.01)
(Continued)

(52) U.S. Cl.
CPC .......... *A61H 23/02* (2013.01); *A61H 39/002* (2013.01); *A61N 1/32* (2013.01); *A61N 1/36* (2013.01);
(Continued)

(58) Field of Classification Search
CPC .................. A61H 23/02; A61H 39/002; A61H 2201/0153; A61H 2201/0157;
(Continued)

(56) References Cited

U.S. PATENT DOCUMENTS

| 1,051,427 A | * | 1/1913 | McCluskey | ......... | F16L 37/0925 |
| | | | | | 403/292 |
| 1,723,306 A | * | 8/1929 | Sipe | ........................ | E04B 1/615 |
| | | | | | 52/396.04 |

(Continued)

FOREIGN PATENT DOCUMENTS

| CN | 203842179 U | * | 9/2014 |
| CN | 203842179 U | | 9/2014 |

(Continued)

OTHER PUBLICATIONS

EPO Form 1507S Search Result for EP 19886825.9.

*Primary Examiner* — Justine R Yu
*Assistant Examiner* — Benjamin M. Kusiak
(74) *Attorney, Agent, or Firm* — Scully, Scott, Murphy & Presser, P.C.

(57) ABSTRACT

A neck massaging device includes an elastic arm, a handle, a connecting member, an electrode assembly, and an electric pulse generating device. The handle includes a first outer shell and a first inner shell. The first outer shell includes a connecting end and a free end opposite to the connecting end, and the first inner shell is buckled with the first outer shell. The connecting member is for connecting the handle to the elastic arm. The connecting member is connected to the connecting end of the handle and buckled with the first inner shell. The electric pulse generating device is electrically connected with the electrode assembly. The free end of the handle may swing with the connecting member as a pivot (Continued)

under an action of external force to drive the first inner shell to be separated from the connecting member.

17 Claims, 5 Drawing Sheets

(51) Int. Cl.
*A61H 39/00* (2006.01)
*A61N 1/32* (2006.01)

(52) U.S. Cl.
CPC ....... *A61N 1/3604* (2017.08); *A61N 1/36014* (2013.01); *A61N 1/36021* (2013.01); *A61H 2201/0153* (2013.01); *A61H 2201/0157* (2013.01); *A61H 2201/10* (2013.01); *A61H 2201/1207* (2013.01); *A61H 2201/165* (2013.01); *A61H 2201/1609* (2013.01); *A61H 2201/1611* (2013.01); *A61H 2201/1645* (2013.01); *A61H 2205/04* (2013.01)

(58) Field of Classification Search
CPC ........ A61H 2201/10; A61H 2201/1207; A61H 2201/1609; A61H 2201/1611; A61H 2201/1645; A61H 2201/165; A61H 2205/04; A61H 2201/169; A61H 2201/5025; A61N 1/32; A61N 1/36; A61N 1/36014; A61N 1/36021; A61N 1/3604; A61N 1/18; A61N 1/0452; A61N 1/0492; A61N 1/22; A63B 2213/004
USPC .......................................................... 601/15
See application file for complete search history.

(56) References Cited

U.S. PATENT DOCUMENTS

| | | | | |
|---|---|---|---|---|
| 7,021,019 | B2* | 4/2006 | Knauseder | E04F 15/04 24/297 |
| 9,010,067 | B2* | 4/2015 | Baker | E04F 15/04 52/391 |
| 2005/0059909 | A1* | 3/2005 | Burgess | A61H 11/00 601/79 |
| 2009/0118652 | A1* | 5/2009 | Carlucci | A61H 7/007 601/134 |
| 2012/0023785 | A1* | 2/2012 | Barnes | A61F 5/14 36/141 |
| 2012/0087741 | A1* | 4/2012 | Desmeules | E02D 27/12 405/253 |
| 2018/0042815 | A1* | 2/2018 | Tang | A61H 39/086 |
| 2018/0272118 | A1* | 9/2018 | Goldwasser | A61N 1/0492 |
| 2019/0046787 | A1* | 2/2019 | Tyler | A61N 1/0492 |
| 2019/0125479 | A1* | 5/2019 | Float | G01L 1/00 |
| 2019/0262212 | A1* | 8/2019 | Schroeder | A61H 1/0296 |
| 2021/0137774 | A1* | 5/2021 | Quan | A61H 15/0078 |

FOREIGN PATENT DOCUMENTS

| | | | | |
|---|---|---|---|---|
| CN | 204106848 U | * | 1/2015 | |
| CN | 204106848 U | | 1/2015 | |
| CN | 108379738 A | | 8/2018 | |
| CN | 108653916 A | | 10/2018 | |
| CN | 108721775 A | | 11/2018 | |
| CN | 108837325 A | * | 11/2018 | ............ A61H 39/00 |
| CN | 108837325 A | | 11/2018 | |
| WO | WO-2017201525 A1 | * | 11/2017 | ............ A61M 21/02 |

* cited by examiner

NECK MASSAGING DEVICE

The present disclosure claims priority to the Chinese Patent Application No. 201811394788.3, filed to the Patent Office of the People's Republic of China on 21 Nov. 2018 and entitled "NECK MASSAGING DEVICE", which is incorporated in the present disclosure by reference in its entity.

FIELD

The present disclosure relates to a massaging device and, more particularly, to a massaging device for neck.

BACKGROUND

In recent years, due to work and bad living habits, cervical spondylosis has youth-oriented tendency.

An existing neck massaging device is worn on the neck, and the neck massaging device includes a main body, a left handle and a right handle, the main body is provided with an electric pulse generating device and an electrode assembly, the left handle and the right handle are movably connected to two sides of the main body, i.e., the left handle and the right handle may swing with joints as fulcrums, and clamping force is provided by springs arranged between the left and right handles and the main body.

When the above-mentioned neck massaging device is implemented and used, the following problems are found to be existed. The existing neck massaging device has a main body of a rigid anti-deformation structure to ensure that an electric pulse generating device may not be damaged, and therefore, the neck massaging device may not be well adapted to the size of the neck of the wearer.

SUMMARY

The present disclosure may aim to provide a neck massaging device adapting to the size or dimension of the neck of a wearer.

According to an embodiment of the present disclosure, a neck massaging device may be provided, which may include an elastic arm, a handle, a connecting member, an electrode assembly, and an electric pulse generating device. The handle includes a first outer shell and a first inner shell. The first outer shell includes a connecting end and a free end opposite to the connecting end, and the first inner shell is buckled with the first outer shell. The connecting member is for connecting the handle to the elastic arm. The connecting member is connected to the connecting end of the handle and buckled with the first inner shell. The electric pulse generating device is electrically connected with the electrode assembly. The free end of the handle may swing with the connecting member as a pivot under an action of external force to drive the first inner shell to be separated from the connecting member.

According to an embodiment of the present disclosure, the electric pulse generating device may be arranged in one of the first outer shell, is far away from the connecting end, and is close to the free end.

According to an embodiment of the present disclosure, the connecting member may include a collar; a first group of connecting sheets connected to the connecting end of the first outer shell of the handle; a second group of connecting sheets connected to the elastic arm. The first group second groups of connecting sheet may extend from the collar to both sides of the collar. A clamping block and a clamping hook may be disposed on the first inner shell, the clamping block is engaged to the collar, and a clamping groove engageable with the clamping hook is formed in the first outer shell.

According to an embodiment of the present disclosure, a positioning strip may be disposed on the first outer shell. The clamping groove and the positioning strip may be arranged around the electric pulse generating device. The first inner shell may be provided with a positioning groove in which the clamping block is embedded.

According to an embodiment of the present disclosure, the first group of connecting sheets may include two first connecting sheets spaced apart from each other. And a first gap may be formed between the two first connecting sheets, through which the clamping block is clamped into the collar.

According to an embodiment of the present disclosure, the second group of connecting sheets may include two second connecting sheets spaced apart from each other. And a second gap may be formed between the two second connecting sheets. The first gap and the second gap may be communicated with an inner space of the collar.

According to an embodiment of the present disclosure, the electrode assembly may be electrically connected to the electric pulse generating device through a conducting wire. The conducting wire may be connected to the elastic arm from the handle and passes through the first gap, the collar and the second gap in sequence.

According to an embodiment of the present disclosure, the elastic arm may include a second outer shell connected to the second group of connecting sheets and a second inner shell buckled with the second outer shell.

According to an embodiment of the present disclosure, an extending length of the first group of connecting sheets from the collar may be unequal to an extending length of the second group of connecting sheets from the collar.

According to an embodiment of the present disclosure, a projection may be disposed on each end of the first outer shell and the second outer shell, which is facing the collar. The projections may be borne against each other and embedded into the collar.

The neck massaging device according to the present disclosure may be worn by the deformation of the elastic arm to well adapt to the size or dimension of the neck of a wearer. In addition, the first outer shell and the first inner shell of the handle may be assembled under the assistance of the collar of the connecting member. During disassembly, the first inner shell may be separated from the collar by only pulling outwards the handles manually by the slight deformation of the first outer shell. Therefore, it is very easy to disassemble accordingly. In addition, the connecting member may be a metal piece to be stronger than the first outer shell. In this way, the life of the product may be prolonged when the first inner shell is locked on the connecting member.

BRIEF DESCRIPTION OF THE DRAWINGS

In order to explain the technical solutions in the embodiments of the present disclosure or the prior art more clearly, the drawings used by the description of the embodiments or the prior art will be briefly introduced below. Obviously, the drawings in the following description may be merely some embodiments of the present disclosure. For those of ordinary skilled in the art, other drawings may be obtained according to the structures shown in the drawings without creative effort, in which.

DETAILED DESCRIPTION

In the following, the technical solutions in the embodiments of the present disclosure will be clearly and completely described with reference to the drawings in the embodiments of the present disclosure. Obviously, the described embodiments may be only a part of the embodiments of the present disclosure, but not all of the embodiments. Based on the embodiments of the present disclosure, all other embodiments obtained by those of ordinary skilled in the art without creative effort shall fall within the protection scope of the present disclosure.

In addition, descriptions such as "first" and "second" in the present disclosure may be for descriptive purposes only, and cannot be understood as indicating or implying the relative importance or implicitly indicating the number of indicated technical features. Therefore, the features defined as "first" and "second" may explicitly or implicitly include at least one of the features. In the description of the present disclosure, the meaning of "a plurality of" may be at least two, for example, two, and three and so on, unless it may be specifically defined otherwise.

According to the present disclosure, the terms "connection", "fixing" and the like should be understood in a broad sense unless otherwise specified and defined, for example, "fixing" may be fixed connection or detachable connection or an integral whole, may be mechanical connection or electrical connection, may be direct connection or indirect connection through an intermediate medium, and may be internal connection of two elements or interaction between two elements, unless it may be clearly defined otherwise. For those of ordinary skilled in the art, the specific meanings of the above terms in the present disclosure may be understood according to specific situations.

In addition, the technical solutions between the various embodiments of the present disclosure may be combined with each other, but must be based on what may be achieved by those of ordinary skilled in the art. When the combination of technical solutions conflicts or cannot be achieved, such a combination of technical solutions should be considered to be nonexistent and not within the scope of protection claimed by the present disclosure.

A neck massaging device 10 according to an embodiment of the present disclosure will be described with reference to FIGS. 1-7 in the following.

Figure 1:
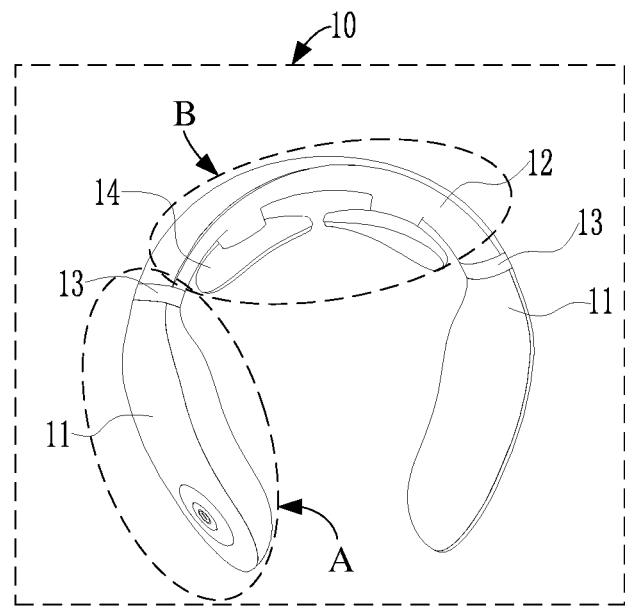
FIG. 1 is a perspective view of a neck massaging device according to an embodiment of the present disclosure.
Figure 2:
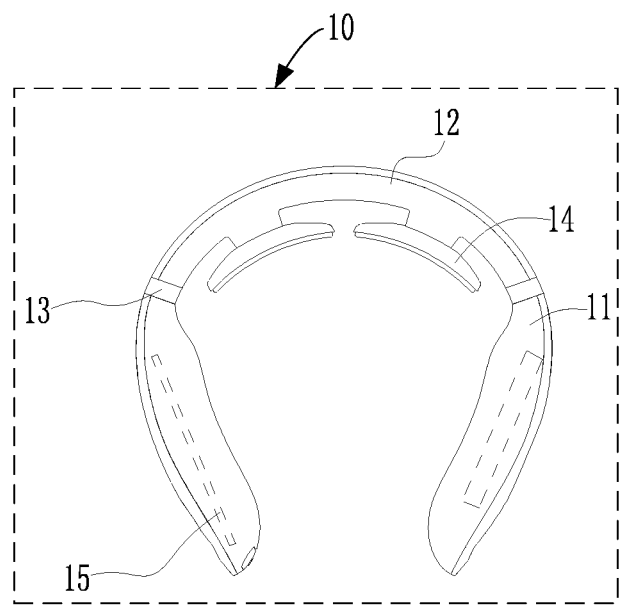
FIG. 2 is a front view of the neck massaging device shown in FIG. 1.

As shown in FIG. 1 and FIG. 2, the neck massaging device 10 may include two handles 11, an elastic arm 12, two connecting member 13, at least two electrode assemblies 14 and an electric pulse generating device 15. The two handles 11 may be fixedly connected to two sides of the elastic arm 12 through the connecting member 13. The two electrode assemblies 14 may be symmetrically arranged on the elastic arm 12. The electrode assemblies 14 may be electrically connected with the electric pulse generating device 15.

Figure 3:
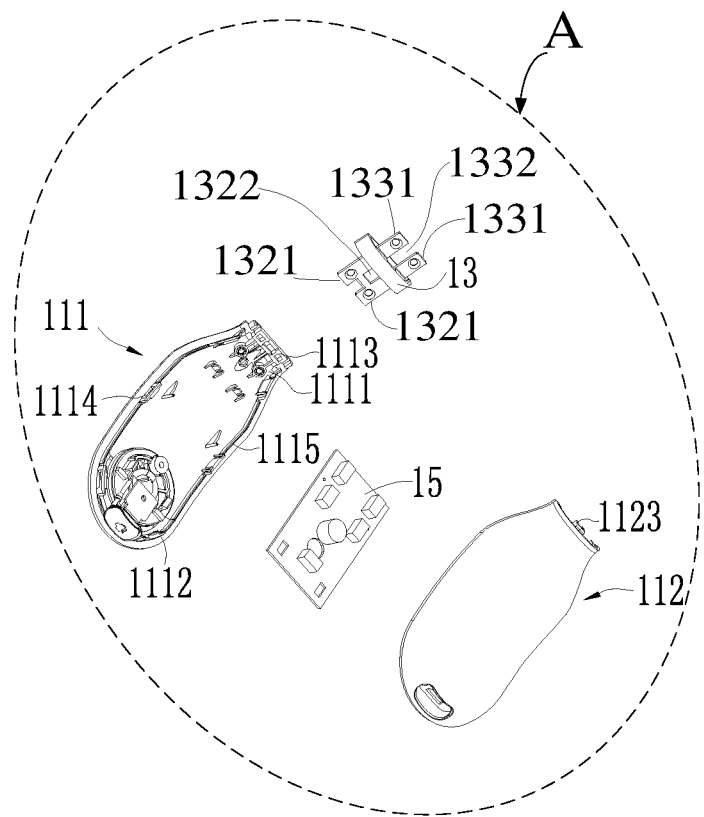
FIG. 3 is an exploded view of one of handles and connecting member shown in FIG. 1.
Figure 4:
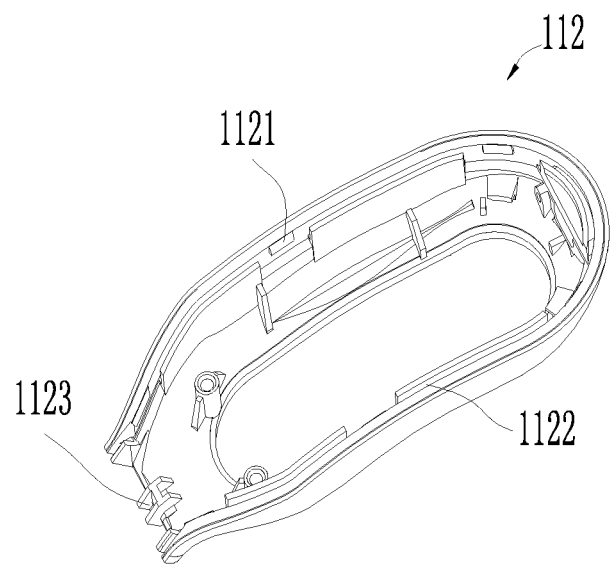
FIG. 4 is a perspective view from another angle of the first inner shell shown in FIG. 3.

As shown in FIG. 3 and FIG. 4, each of the handles 11 may include a first outer shell 111 and a first inner shell 112 buckled with the first outer shell 111. The first outer shell 111 may include a connecting end 1111 and a free end 1112 opposite to the connecting end 1111. The connecting end 1111 may be connected with the connecting member 13 by screws. The connecting end 1111 may be slightly bent. When the handle 11 is pulled outwards by external force, the connecting end 1111 may be slightly deformed, so that the free end 1112 may slightly swing with the connecting member 13 as a pivot. The electric pulse generating device 15 may be arranged on the first outer shell 111 of one of the handles, in a way of being far away from the connecting end 1111 and being close to the free end 1112, to be better protected. A first projection 1113, a plurality of clamping grooves 1114 and a positioning strip 1115 may be disposed on the first outer shell 111. The clamping grooves 1114 and the positioning strips 1115 may be arranged around the electric pulse generating device 15. The first projection 1113 may protrude towards one side of the connecting member 13 and be matched with the connecting member 13. Clamping hooks 1121, a positioning slot 1122 and a clamping block 1123 may be disposed on the first inner shell 12. The clamping hooks 1121 may be fitted into the clamping grooves 1114. The positioning strip 1115 may be embedded in the positioning slot 1122. The position of the clamping block 1123 may be arranged corresponding to the connecting end 1111 of the first outer shell 111. In addition, the first inner shell 112 is further clamped with the connecting member 13.

Figure 5:
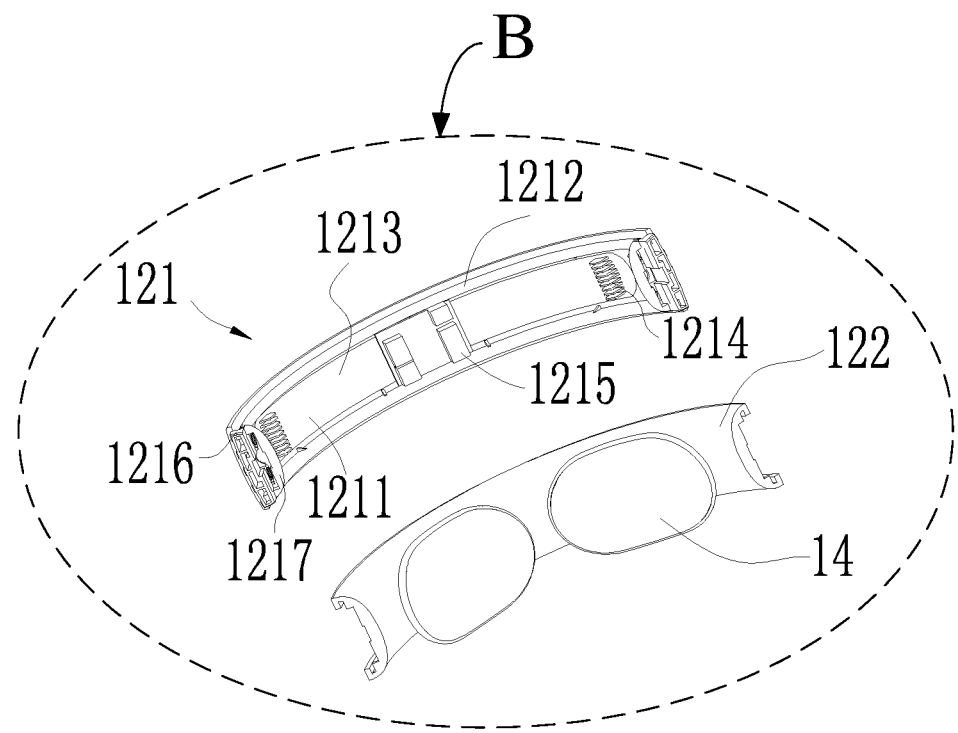
FIG. 5 is an exploded view of an elastic arm and electrode assemblies shown in FIG. 1.

As shown in FIG. 5, the elastic arm 12 may include a second outer shell 121 and a second inner shell 122 buckled with the second outer shell 121. The second outer shell 121 may be made of plastic. The second outer shell 121 may be connected to the connecting member 13 by screws. The second outer shell 121 may be shaped as a bent strip to be elastically deformed. The second outer shell 121 may include an inner wall 1211 and two ridges 1212 arranged on the inner wall 1211 in parallel. A groove 1213 defining accommodating space for conducting wires may be surrounded by the two ridges 1212. At least one line slots 1214 and supporting ribs 1215 may be disposed on the inner wall 1211. The conducting wires may be clamped in the line slots 1214 to be arranged in order. The second inner shell 1220 may be made of silicone rubber to be more skin-friendly. However, a "denting" phenomenon may easily occur. The supporting ribs 1215 may support the second inner shell 122, so that the "denting" phenomenon may be avoided. Further, a second projection 1216 and clamping rings 1217 may be disposed on the second outer shell 121. The second projection 1216 may be arranged at the side of the second outer shell 121 facing the connecting member 13. The second projection 1216 and the clamping rings 1217 may be engaged to the connecting member 13.

Figure 6:
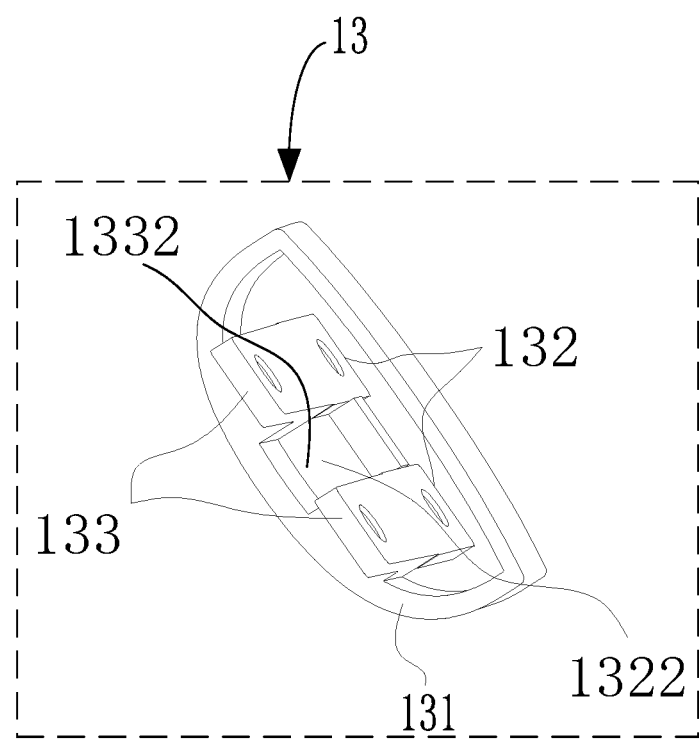
FIG. 6 is a perspective view of the connecting member shown in FIG. 1.
Figure 7:
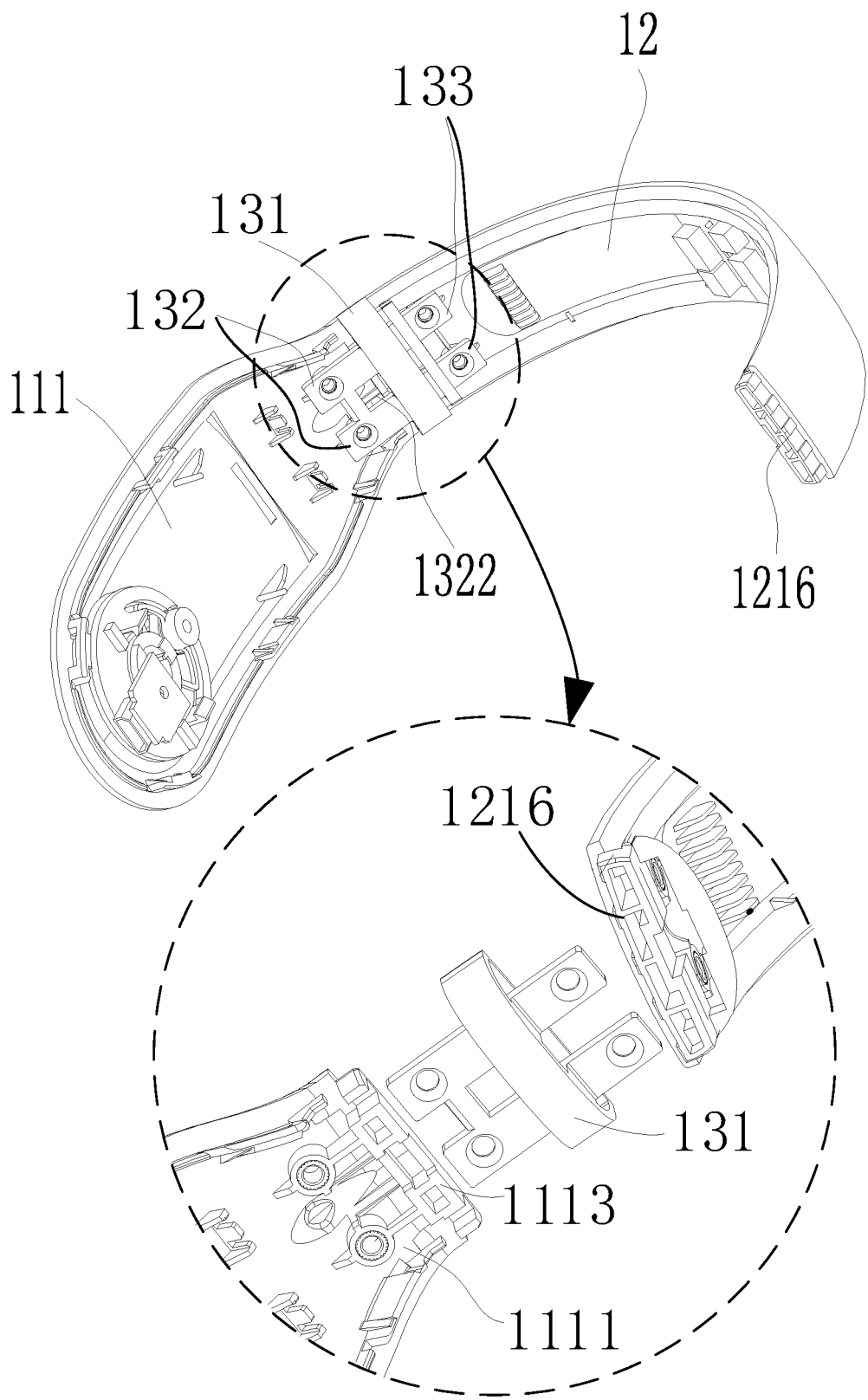
FIG. 7 is a schematic view of connection of a first outer shell, a second outer shell and the connecting member.

As shown in FIG. 6 and FIG. 7, each of the connecting member 13 may include a collar 131, a first group of connecting sheets 132 and a second group of connecting sheets 133. The first group of connecting sheets 132 and the second group of connecting sheets 133 may be configured to be extended from the collar to two sides. The first group of connecting sheets 132 may be connected with the connecting end of the first outer shell 111 of the handle 11. The second group of connecting sheets 133 may be connected with the second outer shell 121 of the elastic arm 12. The second group of connecting sheets 133 may be guided by the clamping ring 1217 to pass therethrough. The first projection 1113 and the second projection 1216 may be borne against each other and embedded into the collar 131. The first projection 1113 may be borne against between an inner wall of the collar 131 and the first group of connecting sheets 132. The second projection 1216 may be borne against between an inner wall of the collar 131 and the second group of connecting sheets 133. By arranging the first projection 1113 and the second projection 1216, the connection strength among the first outer shell 111, the second outer shell 121 and the connecting member 13 may be improved. The first group of connecting sheets 132 and the second group of connecting sheets 133 may be located on the same plane, so that the first projection 1113 and the second projection 1216 may be borne against each other and embedded in the collar 131. An extending length of the first group of connecting sheets 132 from the collar 131 is unequal to an extending length of the second group of connecting sheets 133 from the collar 131. In this way, it may be avoided that the collar 131 is reversely mounted when the product is assembled. Each of the first group of connecting sheets 132 may include two first connecting sheets 1321 spaced apart from each other, and a first gap 1322 may be formed between the two first connecting sheets 1321. Each of the second group of connecting sheets 133 may include two second connecting sheets 1331 spaced apart from each other, and a second gap 1332 may be formed between the two second connecting sheets 1331. The first gap 1322 and the second gap 1332 are communicated with an inner space of the collar 131. In this way, it is convenient for the conducting wires (not shown) to reach the groove 1213 of the elastic arm 12 from the handle 11 passing through the first gap 1322, the collar 131 and the second gap 1332 respectively. That is, the conducting wires passing through the collar 131 may be shielded by the collar 131. In addition, the clamping block 1123 may be clamped into the collar 131 through the first gap 1322. Alternatively, the connecting member 13 is a metal ring.

The electrode assemblies 14 as a long shape may be arranged on the second inner shell 122 of the elastic arm 12 in the extending direction of the elastic arm 12. In this way, the electrode assemblies 14 may be better attached to the neck of the wearer, and the acmesthesia feeling caused by the electrode assembly 14 occasionally when detaching from the skin may be avoided.

When the handles 11 and the elastic arm 12 may be mounted, the electric pulse generating device 15 may firstly be mounted on the first outer shell 111 of one of the handles 11. Secondly the second group of connecting sheets 133 of the connecting member 13 may pass through the clamping rings 1217, and connected with the second outer shell 121 of the elastic arm 12 by screw. And the second projection 1216 may be embedded in the collars 131. And then, the first projection 1113 of the first outer shell 111 and the second projection 1216 may be embedded in the collars 131 after bearing against each other. The first group of connecting sheets 132 may be connected to the first outer shell 111 by screw. Next, the clamping blocks 1123 of the first inner shell 112 of the handles 11 may be clamped into the collars 131 through the first gaps 1322. Finally, the clamping hooks 1121 may be clamped into the clamping grooves 1114, and the positioning strips 1115 may be embedded in the positioning slots 1122. In this case, the mounting of the handles 11 and the elastic arm 12 may be completed.

When the handles 11 and the elastic arm 12 may be disassembled, the two handles 11 may firstly be outwards pulled by external force, accordingly the connecting ends 1111 may be slightly deformed, so that the free ends 1112 may swing with the connecting member 13 as a pivot and drive the first inner shell 112 to move towards a direction far away from the connecting member 13. Secondly, the handles 11 may be further outwards pulled by external force until the clamping blocks 1123 of the first inner shell 112 are separated from the collars 131. And then, the clamping hooks 1121 may be separated from the clamping grooves 1114 by external force. Finally, the first outer shell 111 and the second outer shell 121 may be disassembled from the connecting member 13.

The neck massaging device 10 according to the present disclosure may be worn by the deformation of the elastic arm 12 to well adapt to the size or dimension of the neck of a wearer. In addition, the first outer shell 111 and the first inner shell 112 of the handle 11 may be assembled under the assistance of the collar 131 of the connecting member. During disassembly, the first inner shell 112 may be separated from the collar 131 by only pulling outwards the handles 11 manually by the slight deformation of the first outer shell 111. Therefore, it is very easy to disassemble accordingly. In addition, the connecting member 13 may be a metal piece to be stronger than the first outer shell 111. In this way, the life of the product may be prolonged when the first inner shell 112 is locked on the connecting member 13.

The above descriptions may be only preferred embodiments of the present disclosure, and thus do not limit the patent claims of the present disclosure. Any equivalent structural transformation made by using the description and drawings of the present disclosure under the concept of the present disclosure, or direct/indirect application in other related technical fields may be included in the patent protection scope of the present disclosure.

The invention claimed is:
1. A neck massaging device, comprising:
an elastic arm;
a handle comprising a first outer shell and a first inner shell buckled with the first outer shell, wherein the first outer shell comprises a connecting end and a free end opposite to the connecting end;
a connecting member for connecting the handle to the elastic arm, wherein the connecting member is connected to the connecting end of the handle and buckled with the first inner shell, and the connecting member comprises:
a collar;
a first group of connecting sheets connected to the connecting end of the first outer shell of the handle;
a second group of connecting sheets connected to the elastic arm, wherein
the first and second groups of connecting sheet extend from the collar to two sides of the collar, wherein
a clamping block and a clamping hook are disposed on the first inner shell, the clamping block is engaged to the collar, and a clamping groove engageable with the clamping hook is formed in the first outer shell;
an electrode assembly; and
an electric pulse generating device electrically connected with the electrode assembly, wherein
the free end of the handle swings with the connecting member as a pivot under an action of external force to drive the first inner shell to be separated from the connecting member; and
the first group of connecting sheets and the second group of connecting sheets are located on a same plane.

2. The neck massaging device according to claim 1, wherein the electric pulse generating device is arranged in the first outer shell, is far away from the connecting end, and is close to the free end.

3. The neck massaging device according to claim 1, wherein a positioning strip is disposed on the first outer shell, wherein the clamping groove and the positioning strip are arranged around the electric pulse generating device, and the first inner shell is provided with a positioning groove in which the clamping block is embedded.

4. The neck massaging device according to claim 1, wherein the first group of connecting sheets comprises two first connecting sheets spaced apart from each other, and a first gap is formed between the two first connecting sheets, through which the clamping block is clamped into the collar.

5. The neck massaging device according to claim 4, wherein the second group of connecting sheets comprises two second connecting sheets spaced apart from each other, and a second gap is formed between the two second connecting sheets, wherein
 the first gap and the second gap are communicated with an inner space of the collar.

6. The neck massaging device according to claim 5, wherein the electrode assembly is electrically connected to the electric pulse generating device through a conducting wire, wherein
 the conducting wire is connected to the elastic arm from the handle and passes through the first gap, the collar and the second gap in sequence.

7. The neck massaging device according to claim 1, wherein the elastic arm comprising:
 a second outer shell connected to the second group of connecting sheets; and
 a second inner shell buckled with the second outer shell.

8. The neck massaging device according to claim 1, wherein an extending length of the first group of connecting sheets from the collar is unequal to an extending length of the second group of connecting sheets from the collar.

9. The neck massaging device according to claim 7, wherein a projection is disposed on each end of the first outer shell and the second outer shell, which is facing the collar.

10. The neck massaging device according to claim 7, wherein the second outer shell is made of plastic.

11. The neck massaging device according to claim 7, wherein the second outer shell comprises an inner wall and two ridges arranged on the inner wall in parallel, and a groove defining accommodating space for conducting wires is surrounded by the two ridges.

12. The neck massaging device according to claim 11, wherein at least one line slot and supporting ribs are disposed on the inner wall, the conducting wires are clamped in the at least one line slot to be arranged in order, and the supporting ribs support the second inner shell.

13. The neck massaging device according to claim 7, wherein the second inner shell is made of silicone rubber.

14. The neck massaging device according to claim 7, wherein the first outer shell is provided with a first projection, the first projection protrudes towards the first group of connecting sheets, the second outer shell is provided with a second projection, and the second projection protrudes towards the second group of connecting sheets;
 wherein the first projection and the second projection are borne against each other and embedded into the collar.

15. The neck massaging device according to claim 1, wherein the connecting member is made of metal.

16. The neck massaging device according to claim 1, wherein the electrode assembly is implemented as at least two electrode assemblies, and each of the at least two electrode assemblies as a long shape is arranged on the second inner shell of the elastic arm in an extending direction of the elastic arm.

17. The neck massaging device according to claim 1, wherein the connecting end is connected with the connecting member by screws.

* * * * *